(12) United States Patent
Harvie

(10) Patent No.: US 8,939,923 B2
(45) Date of Patent: Jan. 27, 2015

(54) OXYGEN HEALING SYSTEM AND METHOD OF USE

(76) Inventor: Mark R. Harvie, Milton, VT (US)

(*) Notice: Subject to any disclaimer, the term of this patent is extended or adjusted under 35 U.S.C. 154(b) by 189 days.

(21) Appl. No.: 13/585,857

(22) Filed: Aug. 15, 2012

(65) Prior Publication Data

US 2013/0042877 A1 Feb. 21, 2013

Related U.S. Application Data

(60) Provisional application No. 61/575,268, filed on Aug. 18, 2011.

(51) Int. Cl.
*A61F 5/00* (2006.01)

(52) U.S. Cl.
USPC ............................................. 602/13; 128/885

(58) Field of Classification Search
CPC .......... A62B 7/14; A62B 9/02; A62B 17/008; A62B 18/04; A62B 7/10; A62B 9/022; A62B 9/027; B64D 10/00; B64D 2010/002; B64D 2010/005; F16K 17/0473; A61F 2250/0067; A61F 2250/0068; A61F 2/0077; A61F 2/16; B63C 9/1255; B63C 2009/042; B63C 9/1055; B63C 9/155; B63C 11/30; B63C 2009/085; B63C 9/08; B63C 9/24; B63C 2009/0094; B63C 2009/044; B63C 2009/131; B63C 9/0005; B63C 9/02; B63C 9/04; B63C 9/065; B63C 9/105; B64B 1/02; B64B 1/06
USPC .......... 602/13, 19; 128/202.19, DIG. 20, 885, 128/886
See application file for complete search history.

(56) References Cited

U.S. PATENT DOCUMENTS

| | | | | |
|---|---|---|---|---|
| 2,954,569 A | * | 10/1960 | McCord et al. | 114/344 |
| 3,107,678 A | * | 10/1963 | Still | 128/202.19 |
| 2004/0033739 A1 | * | 2/2004 | Courtney | 441/88 |

* cited by examiner

*Primary Examiner* — Michael A. Brown
(74) *Attorney, Agent, or Firm* — Eric R. Benson, Esq.

(57) ABSTRACT

This invention relates to a pressure related ulcer and perineal dermatitis prevention and treatment device and method of use. The device may be used in conjunction with a urine collection and disposal system that would be beneficial for incontinent users. In use the device forms an automatic pressure controlled topical hyperbaric oxygen chamber and further incorporates a flexible inflated tube system that is controlled by a microprocessor to relief pressure on affected areas of a user's body and provide circulation stimulating therapeutic massage. When used by incontinent persons the device automatically removes expressed urine to minimize additional risk factors known to cause or exacerbate pressure related ulcers and perineal dermatitis.

14 Claims, 3 Drawing Sheets

OXYGEN HEALING SYSTEM AND METHOD OF USE

CROSS REFERENCE TO RELATED APPLICATION

This Application claims priority from the Applicant's Provisional Patent Application No. 61/575,268 which was filed on Aug. 18, 2011.

BACKGROUND ART

Pressure ulcers, or PRUs, and perineal dermatitis that often lead to PRUs have affected humans throughout history and addressing the management of these pressure ulcers is now a prominent healthcare issue in the United States and elsewhere in the world. A PRU which is also known as a pressure sore is a lesion that develops on the skin and underlying tissues from the unrelieved pressure that occurs usually over a bony prominence. All skin and body tissues rely on an adequate blood supply for oxygen and nutrients. When these tissues are compressed for an extended period from hours to days, the critical blood supply can be cut off which then leads to development of a PRU. Despite advances in nursing care, surgery, medical procedures and education, pressure ulcers remain to this day to be a major cause of morbidity and mortality. This is particularly true for persons with impaired sensation, advanced age or prolonged immobility. Consequently, more than one million PRUs occur in the United States annually.

The incidence of PRUs among hospitalized patients ranges from a low of 2.7% to 29%. The prevalence among hospitalized patients, however, is somewhat higher coming in at 3.5% to 69%. Critical care unit patients have an increased risk of pressure ulcers with a 33% incidence rate and 41% prevalence rate respectively. Hospital admitted elderly patients receiving non-elective orthopedic procedures, such as hip replacements and or treatment of bone fractures are at even greater risk with a 66% incidence rate.

The rate of PRUs in the nursing home environment is in the range of 2.6% to 24%. The incidence is 25% however among residents of acute care hospitals. Patients with preexisting pressure ulcers have a 26% incidence of secondary PRU formation in the subsequent 6-month period following the first incidence. Interestingly while the rate of PRUs in chronic care hospitals is 10.8%, a full 33% of those admitted to a chronic care hospital already have pressure ulcers.

Thankfully with adequate treatment most PRUs heal within a year. Despite that fact, however, about 60,000 people die each year in the United States alone from complications of PRUs. In fact a person that has developed a PRU has a 4.5 times greater risk of death than a person with the identical risk factors but does not have a PRU. Additionally there can arise a secondary complication, wound related bacteremia (i.e. sepsis), and this factor can further increase the risk of mortality up to 55%.

A significant number of the patients who are elderly and/or immobile and susceptible to PRUs are also incontinent. It is well known in the art that incontinence significantly increases the risk of the development of PRUs. The increased risk stems from the chemical and/or physical effects that residual urine has on the skin. Urine typically is composed of 95% water and 5% organic solutes that are composed of mostly urea ($(NH_2)_2CO$) and smaller amounts of related compounds.

When a patient is incontinent and their excreted urine is not drained away from the body the urinary urea undergoes chemical decomposition on the skin forming ammonium hydroxide ($NH_4OH$), an alkaline substance that raises the skin pH which favors bacterial and fungal proliferation common in both perineal dermatitis and PRUs. It is not uncommon for perineal dermatitis to facilitate the development of PRUs by the concomitant friction and shear related skin breakdown that results from this type of dermatitis making pressure sores more likely. Once a person's skin is chemically compromised by the $NH_4OH$ the abundant ubiquitous levels of microorganisms often result in prolific fungal and bacterial growth on the skin. *Candida albicans* is the most common fungal infectious agent in cases of perineal dermatitis and *Staphylococcous* is the most common bacterial infectious agent in cases of perineal dermatitis. In the event that a pressure sore does develop, *Staphylococcous* and *E-coli* infections of the pressure sore are more common as a result of the chemical effects of urine on the skin. These infections are more serious affecting deeper tissues which can lead to sepsis and ultimately death of untreated or otherwise uncontrolled.

Incontinence also produces direct negative physical effects on the skin. The persistent presence of moisture on the surface of the skin that results from incontinence causes a reduction in the exposed skin's hardness and temperature. These changes increase the vulnerability to pressure induced blood flow reduction that often result in a PRU. Frequent washing and drying after incontinence related "accidents" further aggravates the skin with frictional damage and this in turn adversely effects the barrier function of the skin.

The management of incontinence and pressure area care using absorbent pads is the most common method. However, research has concluded that the use of absorbent incontinence pads ultimately has an adverse effect on the pressure redistributing qualities of specialized support surfaces being used to prevent a PRU in the first place. These pads often have ridges that result from the folding of the pad at the time of packaging by the manufacturer. These ridges contribute to the effect of pressure and development of a PRU.

Market studies have been performed to estimate the costs of treatment and the costs for hospitals stays for patients who developed PRUs during hospitalization. These costs are in excess of $16.0 Billion a year. Particularly, the PRUs among the elderly who are institutionalized are one of the most costly of all diseases to treat. PRUs add over $1.5 billion of expenditures and an additional 2.8 million Medicare hospital days per year to the United States healthcare system. Depending on the stage of development the cost of treatment for PRUs can range from $3,000 to $50,000 per pressure ulcer. Often time reconstructive surgery is needed and these costs have been estimated to exceed $30,000 per patient and rising. These costs alone, without even considering the cost of human suffering, demonstrate the importance of preventing pressure ulcers (PRUs) in the first place and of cost effective treatment practices for PRUs were they to develop.

Much of the cost and current treatment modalities are expensive and labor intensive. This is the proximate result of the cause of the PRU in the first instance, that being the lack of mobility of the patient whose own body weight and lack of movement impede or prevent adequate blood flow to the pressure points of the body in contact with a support surface such as a bed. This can lead to ulceration and necrosis and even death.

The current art treatment modalities addressing the many aspects of PRU care usually require a multidisciplinary approach. Members of a PRU care team may include:
A primary care physician who oversees the treatment plan;
A physician specializing in wound care;
Nurses or medical assistants who provide both care and education for managing wounds;

A social worker who helps a person or family access appropriate resources and addresses emotional concerns related to long-term recovery;
A physical therapist who helps with improving mobility;
A dietitian who assesses nutritional needs and recommends an appropriate diet; and
A neurosurgeon, orthopedic surgeon or plastic surgeon, depending on whether surgery is required and what type of surgery is needed.

Clearly bringing these resources together can be impossible at times depending upon the stresses present in the existing care facility or treatment regimen. Too often in a public urban hospital setting, or low income nursing home environment, etc., a patient may not be moved for many hours if not days at times. Without the frequent relief of the pressure and the therapeutic movement of the body parts prone to PRUs there is little likelihood that such a patient will recover or fully heal from a PRU, especially if their lack of mobility persists for any protracted period of time.

It is widely recognized in the art that the first step in treating a PRU at any stage is relieving the pressure that caused it. The main strategies to reduce pressure include the following:
Repositioning. A person with PRUs needs to be repositioned regularly and placed in correct positions. People confined to a wheelchair should on their own change position as much as possible or at least every 15 minutes if they are able. At a minimum a person in a wheel chair should have assistance with changes in position at least every hour. People that are confined to bed should change positions at least every two hours. The use of lifting devices in these situations is often used to avoid friction during the repositioning.
Support surfaces. There exists in the art many different types of special mattresses, cushions or pads and beds that can help a person lie in a position that will relieve pressure on an existing sore and/or protect vulnerable skin from damage. Additionally there are variety of foam, air-filled or water-filled devices provide cushion for those sitting in wheelchairs. The type of devices used will depend on a person's condition, body type and mobility.

In order to heal properly PRUs need to be free from damaged, dead or infected tissue. Debridement of these tissues is done with various methods the choice of which depends on the severity of the PRU, the general health condition of the patient and the ultimate goal of treatment. Debridement methods include:
1) Autolytic debridement which uses the body's natural process of producing enzymes that break down dead tissue. Analytic debridement can be enhanced with a wound dressing that keeps the PRU moist and clean;
2) Enzymatic debridement which is the use of topical chemical enzymes and dressings engineered to break down dead tissues found in PRUs;
3) Mechanical debridement which uses one of many methods that physically loosen or abrade and remove wound debris. These may include pressurized irrigation devices, whirlpool baths or other specialized dressings;
4) Surgical debridement which involves the cutting away of dead tissue.

The cleaning and dressing of wounds is also quite critical. The care that promotes healing of the wound includes the following:
1) Cleaning is essential to prevent infection. A stage I wound should be gently washed with water and mild soap, however, any open sores should be cleaned with a saline solution each time the dressing is changed.
2) A dressing promotes healing by keeping a wound moist, creating a barrier against infection and keeping the surrounding skin dry. A variety of dressings are appropriate for PRUs, including films, gauzes, gels, foams and various treated coverings. A combination of these dressings may be used.

Pressure sores that fail to heal may require surgical intervention. The goals of surgery include improving the hygiene and appearance of the sore, preventing or treating infection, reducing fluid loss through the wound, and lowering the risk of cancer. The type of reconstruction that's best in any particular case depends mainly on the location of the wound and whether there's scar tissue from a previous operation. In general, though, most pressure wounds are repaired using a pad of the person's own muscle, skin or other tissue to cover the wound and cushion the affected bone (flap reconstruction).

Alternatively PRUs are being treated with a modicum of success with topical hyperbaric oxygen therapy. Oxygen ($O_2$) and their reactive oxygen species are involved in all stages of wound healing such as: modulating cell migration; adhesion; proliferation; neovascularization; remodeling and apoptosis. It is well known in the art of PRU treatment modalities that $O_2$ is vital in the synthesis of collagen, enhancement of fibroblasts, angiogenesis and leukocyte function. Additionally $O_2$ also has key functions in energy metabolism and in the inhibition of microbial growth. As a consequence, tissue hypoxia, caused by disrupted or compromised vasculature, seems to be a key factor that limits PRU healing. Topical oxygen therapies increase the tissue blood oxygenation ($pO_2$) of superficial wound tissue. Superficial $pO_2$ at 2 mm depth at the center of a wound bed can result in an increase of $pO_2$ from less than 10 mm Hg to 40 min Hg in a matter of only a few minutes. Additionally the penetration of oxygen into the tissue of a PRU with topical wound oxygen ($TWO_2$) devices, such as a topical hyperbaric oxygen therapy device can increase the most crucial angiogenesis related growth factor involved in the healing process, vascular endothelial growth factor (VEGF).

The benefits of hyperbaric oxygen therapy are well known in the art. Hyperbaric oxygen has been used topically to treat pressure sores and skin ulcers. Specially constructed devices equipped with controlled pressure seals and automatic relief valves have been used. Typical hyperbaric oxygen therapy uses a constant pressure of generally around 22 mm. Hg (1.03 atmospheres absolute) maintained inside the chamber where the PRU is located using pure oxygen at a flow-rate of 2 to 8 liters per minute with direct discharge to atmosphere. The topical hyperbaric oxygen therapy results in bacterial growth suppression, enhanced granulation, and formation of epithelial cells. However, the vascularisation of the patient being treated does seem to have a direct impact on the success of the treatment. The more vascular the patient, the more successful the outcome. Topical hyperbaric oxygen treatment is typically tolerated well and overall it shortened patients healing time and was also useful in the preparation for plastic surgery repair if needed.

As outlined above incontinence has a direct negative effect on patient outcomes for those being treated for PRUs. The presence of urine and the byproducts of the breakdown of the urea that are present in the urine exacerbate the PRU creating a situation where it is difficult, if not impossible, to heal the effected area.

Clearly there is a long felt need for a device and method of use that would combine the features necessary to at the same time provide an effective urine disposal means in combination with hyberbaric oxygen therapy and skin surface pressure relief and redistribution. There are no such acceptable prior art devices that combine all these features into a safe any easy device to use. While the existing PRU and perineal dermatitis treatment procedures and devices may fulfill their respective particular objectives and requirements, and are most likely quite functional for their intended purposes, it will be noticed that none of the prior art disclose an apparatus or method of use that combines the most effective PRU and perineal dermatitis treatment modalities into one device. As such, there apparently still exists the need for such device, especially considering the 60,000 annual death toll in the United States alone that result from PRUs.

The current invention addresses all of these issues to provide a technology that provides a much more effective, efficient and user friendly device. In this respect, the present invention disclosed herein substantially corrects these problems and fulfills the need for such a device.

DISCLOSURE OF THE INVENTION

In view of the foregoing limitations inherent in the known types of perineal dermatitis and PRU prevention and treatment devices and methods of use now present in the prior art, the present invention provides an apparatus and method of use that has been designed to provide the following features, that may be used individually or in combination, for the benefit of a user:

An effective automatic urine detection and collection means that removes discharged urine thereby preventing prolonged skin contact.

A sealable topical hyperbaric oxygen treatment of perineal dermatitis and pressure related ulcerations.

A series of individually pneumatically controlled pressure chambers engineered to relieve pressure on sites prone to pressure related ulcerations.

A series of sensors engineered to continuously monitor a user's: localized body temperature; blood oxygen saturation; presence of a purulent liquid or bleeding; transcutaneous microvascular dynamics using in vivo optical measurement by laser Doppler fluximetry LDF, pulse oximetry, photoplethysmography (PPG) and/or diffuse reflectance spectroscopy; and the force of pressure on the user's skin being exerted by one or more of the surfaces supporting the user.

A microprocessor that is capable of receiving the data transmitted by the series of sensors and thereby automatically adjusting or accomplishing as needed one or more of the following: the increasing or decreasing the oxygen flow; the pressure or concentration within the hyperbaric chamber to the wound situs; the pressure to be applied to one or more of the pneumatically controlled pressure chambers to change the user's body position and/or pressure on an area indicated by the sensors to be under stress and prone to ulceration; the transmitting of a notification to care personnel of a user condition and/or need of attention; the storage of data with recall and report generation capacity.

These features are improvements which are patently distinct over similar devices and methods which may already be patented or commercially available. As such, the general purpose of the present invention, which will be described subsequently in greater detail, is to provide a field designed apparatus that incorporates the present invention. There are many additional novel features directed to solving problems not addressed in the prior art.

A hip, lower back and gluteal area pressure related ulceration and perineal dermatitis treatment embodiment of incontinent users the device and method of use which incorporates a urine collection and disposal means, a topical hyperbaric oxygen chamber with disposed sensor array with a plurality of variable pressure chambers that are all controlled by a microprocessor with display and data transmission capabilities is disclosed herein and is more particularly illustrated on the attached drawings.

Additionally an embodiment engineered for treating and preventing pressure related ulcerations of continent users or parts of the body not exposed to urine and method of use which incorporates a topical hyperbaric oxygen chamber with disposed sensor array with a plurality of variable pressure chambers that are all controlled by a microprocessor with display and data transmission capabilities is disclosed herein and is more particularly illustrated on the attached drawings.

It would be obvious to one skilled in the art to construct this device in different shapes and sizes. Similarly it would be obvious to manufacture this device or portions of it out of some other material like that of plastic, metal, ceramic or composite.

To attain this in the incontinent user embodiment, the present invention generally comprises seven major components: 1) a urine collection and disposal means; 2) a plurality of flexible inflatable tubes; 3) a plurality of life sign sensors; 4) a compressed oxygen source; 5) a life signs and pressure microprocessor in communication with the life signs sensors functioning as a regulator for the source of oxygen; 6) a plurality of body seals with disposed oxygen ports; and 7) a plurality of attachment strips.

To attain this in the multi-application embodiment, the present invention generally comprises six major components: 1) a plurality of flexible inflatable tubes; 2) a plurality of life sign sensors; 3) a compressed oxygen source; 4) a life signs and pressure microprocessor in communication with the life signs sensors functioning as a regulator for the source of oxygen; 5) a plurality of body seals with disposed oxygen ports; and 6) a plurality of attachment strips.

These together with other objects of the invention, along with the various features of novelty which characterize the invention, will be pointed out with particularity in the claims which will be annexed to and forming a part of the full patent application once filed. For a better understanding of the invention, its operating advantages and the specific objects attained by its uses, reference should be had to the accompanying drawings and descriptive matter in which there is illustrated preferred embodiments of the invention.

BEST MODES FOR CARRYING OUT THE INVENTION

I. Preferred Embodiments

A. Incontinent User Embodiment

Figure 1:
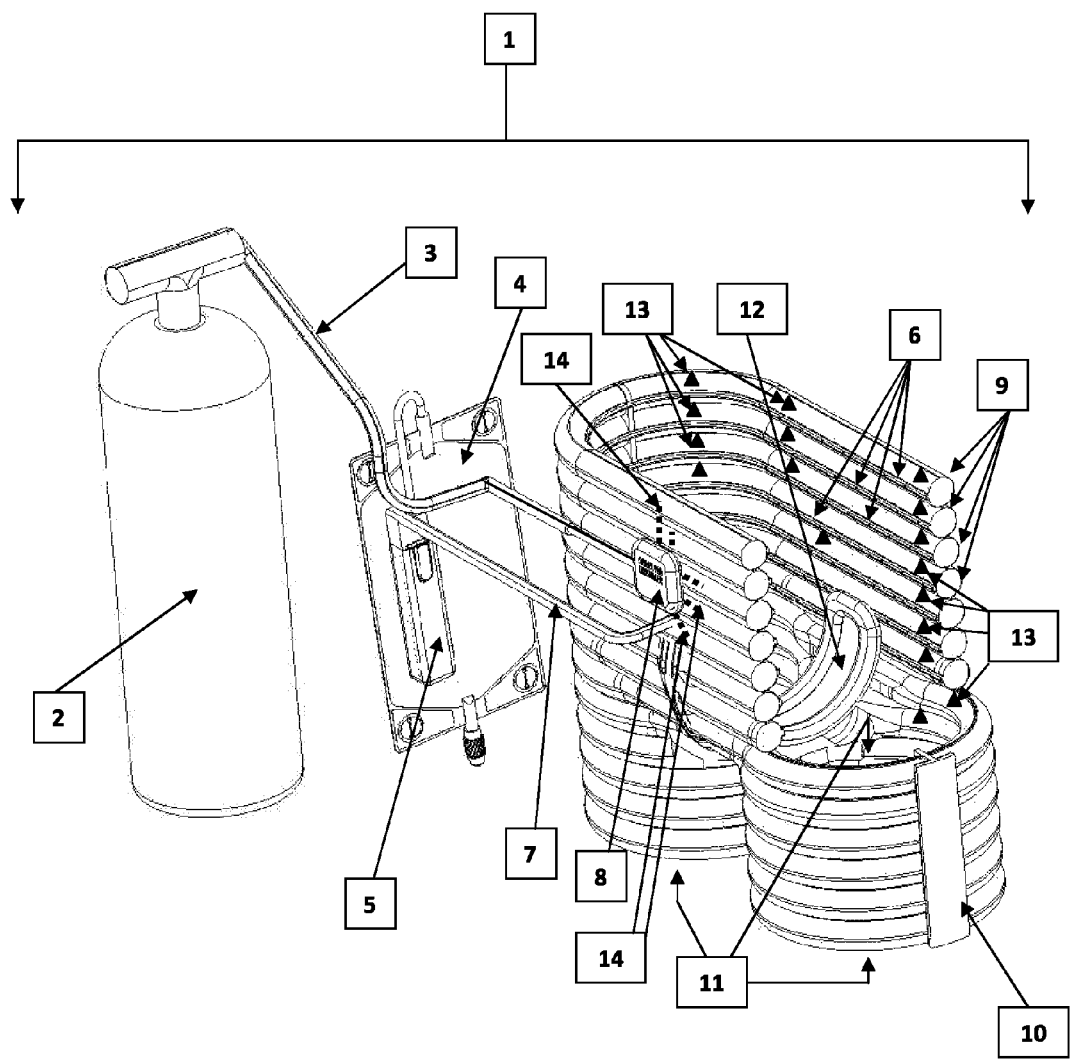
FIG. 1 is a cutaway perspective view of the female version of the incontinent user embodiment of the Oxygen Healing System and Method of Use.
Figure 2:
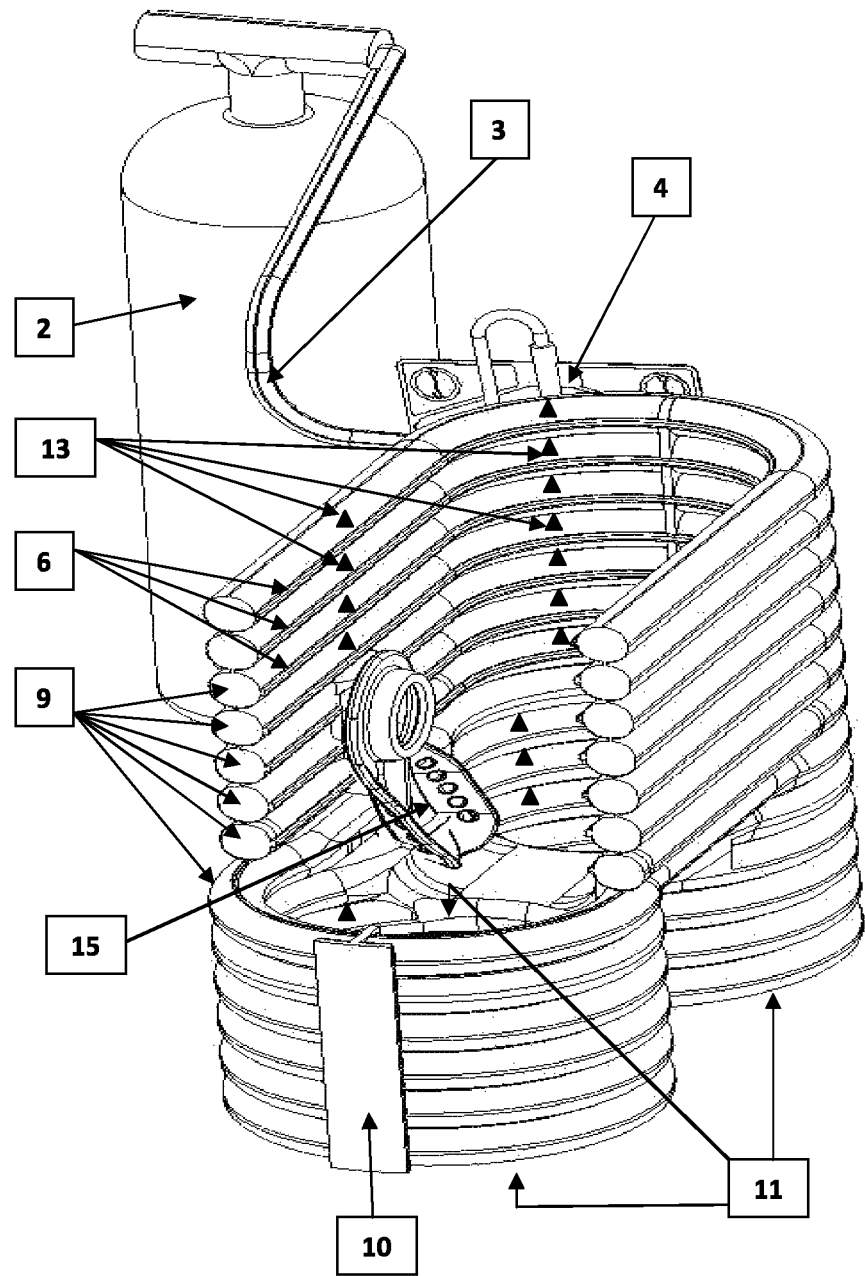
FIG. 2 is a cutaway perspective view of the male version of the incontinent user embodiment of the Oxygen Healing System and Method of Use.

With reference now to the drawings, and in particular to FIGS. 1-2 thereof, a new and novel incontinent user embodiment of the Oxygen Healing System and Method of Use (1) embodying the principles and concepts of the present invention is depicted in these drawings as comprising seven major components: 1) a urine collection and disposal means (12, 7, 4 & 5 in the female version in FIGS. 1 and 15 in the male version in FIG. 2 with 7, 4, & 5 of FIG. 1 not shown in FIG. 2); 2) a plurality of Flexible Inflatable Tubes (9); 3) a plurality of Life Sign Sensors (13); 4) a Compressed Oxygen Source (2); 5) a Life Signs and Pressure Microprocessor (8) in communication with the Life Signs Sensors (13) functioning as a regulator for the Compressed Oxygen Source (2); 6) a plurality of Body Seals with Disposed Oxygen Ports (6); and 7) a plurality of Attachment Strips (10).

GENERAL DESCRIPTION OF REFERENCE NUMERALS IN THE DESCRIPTION AND DRAWINGS

Any actual dimensions listed are those of the preferred embodiment. Actual dimensions or exact hardware details and means may vary in a final product or most preferred embodiment and should be considered means for so as not to narrow the claims of the patent.

LIST AND DESCRIPTION OF COMPONENT PARTS OF THE INVENTION (1) Oxygen Healing System
(2) Compressed Oxygen Source
(3) Oxygen Line
(4) Urine Storage and Disposal Unit
(5) Urine Disposal Control Unit
(6) Body Seals with Disposed Oxygen Ports
(7) Urine Transport Line
(8) Life Signs and Pressure Microprocessor
(9) Flexible Inflatable Tubes
(10) Adjustable Attachment Strip
(11) User's Leg Channels
(12) Female Urine Collector with Sensors
(13) Life Signs Sensor
(14) Interface Oxygen Line
(15) Male Urine Collector with Sensors In the incontinent user embodiment a plurality of interconnected Flexible Inflatable Tubes (9) most likely made from medical grade urethane which are disposed to form a garment similar to a pair of shorts. To use the device a user legs (feet first) enter from the top of the device as depicted in FIGS. 1 & 2 with each leg going through the User's Leg Channels (11). Adjustable Attachment Strips (10) are attached to the device to further secure the device to the body to aid in maintaining beneficial seals of the device to the body. Once on the user like a worn pair of shorts, the user's genitalia will be in functional proximity or contact with the urine collection and detection means (the Female Urine Collector with Sensors (12) for the female version and the Male Urine Collector with Sensors (15) for the male version) In this position in the event a user urinates the expelled urine is contained with the respective urine collection and detection means (the Female Urine Collector with Sensors (12) for the female version and the Male Urine Collector with Sensors (15) for the male version). The presence of urine is detected by the Female Urine Collector with Sensors (12) in the female version and the Male Urine Collector with Sensors (15) in the male version. The urine sensors are in electronic communication with the Urine Disposal Control Unit (5) by means of the Urine Transport Line (6) such that when the presence of urine is detected the Urine Disposal Control Unit (5) is activated initiating a pumping process whereby the urine is then drawn out of the Female Urine Collector with Sensors (12) in the female version and the Male Urine Collector with Sensors (15) in the male version through the Urine Transport Line (6) and deposited into the Urine Storage and Disposal Unit (4). Once all the urine is pumped away from the Female Urine Collector with Sensors (12) in the female version and the Male Urine Collector with Sensors (15) in the male version the urine sensors therein communicate the absence of urine to the Urine Disposal Control Unit (5) which then deactivates the pumping process.

The device worn as depicted in the drawings and as stated above is engineered to function as a topical hyperbaric oxygen chamber capable of applying a user desired maintained pressure which is typically around 22 mm. Hg (1.03 atmospheres absolute) inside the chamber using pure oxygen at a flow-rate of 2 to 8 liters per minute from the Compressed Oxygen Source (2) with direct discharge to atmosphere. To accomplish this positive pressure and delivery of oxygen the device uses a plurality of Body Seals and Disposed Oxygen Ports (6) that are attached to the body contact surface of each of the flexible inflated tubes (9) thereby forming a reasonably tight seal against the user's body. The oxygen pressure is delivered to the Body Seals and Disposed Oxygen Ports (6) from the Compressed Oxygen Source (2) by transporting the compressed oxygen through the Oxygen Line (3) to the Life Signs and Pressure Microprocessor (8) which regulates the pressure in the formed hyperbaric chamber by monitoring the pressure in the chamber by means of the pressure sensor located in the Life Signs Sensor (13) and adding or relieving the pressure to maintain a desired level through the Interface Oxygen Line (14) which also contains the transmission means for the communication between the plurality of Life Signs Sensors (13) and the Life Signs and Pressure Microprocessor (8).

Additionally the Life Signs and Pressure Microprocessor (8) receives data transmitted from the Life Signs Sensors (13) of body and skin conditions that may indicate the formation of a PRU or perineal dermatitis is imminent or that there are conditions of an existing PRU or perineal dermatitis that are being aggravated. The Life Signs Sensors (13) may be comprised of any one or more of the following sensors: body temperature; blood oxygen saturation; presence of a purulent liquid or bleeding; transcutaneous microvascular dynamics using in vivo optical measurement by laser Doppler fluximetry (LDF), pulse oximetry, photoplethysmography (PPG) and/or diffuse reflectance spectroscopy; and the force of pressure on the user's skin being exerted by one or more of the surfaces supporting the user. The Life Signs and Pressure Microprocessor (8) receives a continuous data stream of information from the Life Signs Sensors (13) and evaluates the data for adjustments of the device and/or notification of care personnel. If the Life Signs and Pressure Microprocessor (8) detects a life sign or pressure change in an area at risk of PRU, etc., or in treatment there for, the Life Signs and Pressure Microprocessor (8) can automatically change or pulsate for a massage type motion the oxygen pressure within the Flexible Inflatable Tubes (9) by providing compressed oxygen from the Compressed Oxygen Source (2) through the Oxygen Line (3) through the internal valve and solenoid system in the Life Signs and Pressure Microprocessor (8) through a conduit in the Interface Oxygen Line (14) to the Flexible Inflatable Tubes (9). This process will in effect move and or massage the user to relieve the pressure and stimulate blood flow to the region detected by the device to be a problem. In the event that the device continues to detect the problem or a worsening condition the Life Signs and Pressure Microprocessor (8) will display the problem and simultaneously transmit the data and warning to a remote location such as a nurse's station or over the Internet.

B. Multi-Application Embodiment

Figure 3:
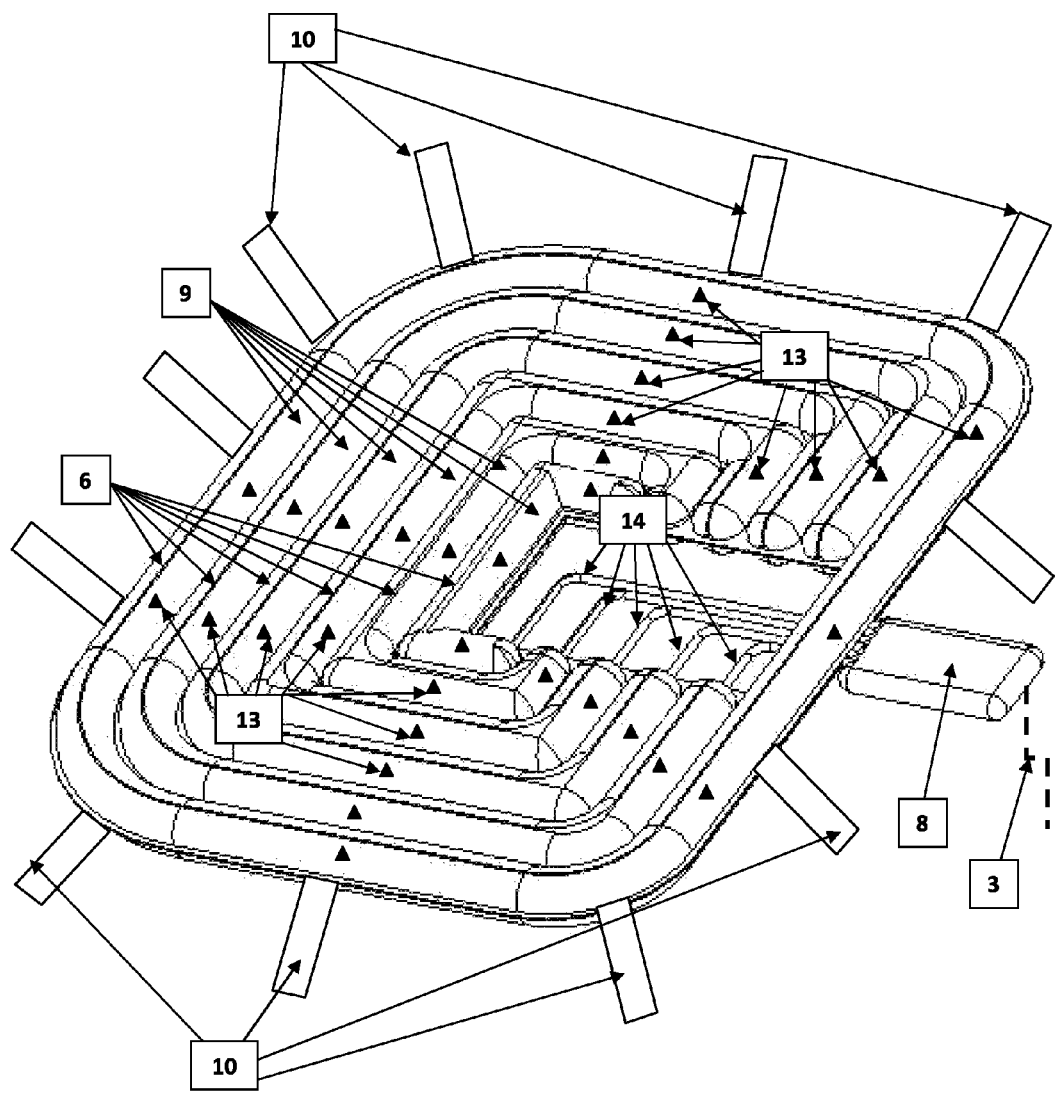
FIG. 3 is a cutaway perspective view of the multi-application embodiment of the Oxygen Healing System and Method of Use.

With reference now to the drawings, and in particular to FIG. 3 thereof, a new and novel multi-application embodiment of the Oxygen Healing System and Method of Use embodying the principles and concepts of the present invention is depicted in these drawings as comprising six major components: 1) a plurality of Flexible Inflatable Tubes (9); 2) a plurality of Life Sign Sensors (13); 3) a Compressed Oxygen Source (2); 4) a Life Signs and Pressure Microprocessor (8) in communication with the Life Signs Sensors (13) functioning as a regulator for the Compressed Oxygen Source (2); 5) a plurality of Body Seals with Disposed Oxygen Ports (6); and 6) a plurality of Attachment Strips (10).

GENERAL DESCRIPTION OF REFERENCE NUMERALS IN THE DESCRIPTION AND DRAWINGS

Any actual dimensions listed are those of the preferred embodiment. Actual dimensions or exact hardware details and means may vary in a final product or most preferred embodiment and should be considered means for so as not to narrow the claims of the patent.

LIST AND DESCRIPTION OF COMPONENT PARTS OF THE INVENTION (1) Oxygen Healing System
(2) Compressed Oxygen Source (not shown in FIG. 3)
(3) Oxygen Line
(6) Body Seals with Disposed Oxygen Ports
(8) Life Signs and Pressure Microprocessor
(9) Flexible Inflatable Tubes
(10) Adjustable Attachment Strip
(13) Life Signs Sensor
(14) Interface Oxygen Line In the multi-application embodiment a plurality of interconnected Flexible Inflatable Tubes (9) most likely made from medical grade urethane which are disposed to form a flexible pad that can be attached topically to a user's body in virtually any location and attached thereto by means of the Adjustable Attachments Strips (10) which can be made of Velcro or some other attachment means. To use the device a user places the device in the desired location and using the Adjustable Attachments Strips (10) the user draws the device against the skin using caution not to draw the Adjustable Attachments Strips (10) too tight and restrict blood flow thereby, but reasonably snug to permit the creation thereby of a hyberbaric oxygen chamber of about 1.03 atmospheres of pressure.

The device affixed the user as stated above is engineered to function as a topical hyperbaric oxygen chamber capable of applying a user desired maintained pressure which is typically around 22 mm. Hg (1.03 atmospheres absolute) inside the chamber using pure oxygen at a flow-rate of 2 to 8 liters per minute from the Compressed Oxygen Source (2) with direct discharge to atmosphere. To accomplish this positive pressure and delivery of oxygen the device uses a plurality of Body Seals and Disposed Oxygen Ports (6) that are attached to the body contact surface of each of the flexible inflated tubes (9) thereby forming a reasonably tight seal against the user's body. The oxygen pressure is delivered to the Body Seals and Disposed Oxygen Ports (6) from the Compressed Oxygen Source (2) by transporting the compressed oxygen through the Oxygen Line (3) to the Life Signs and Pressure Microprocessor (8) which regulates the pressure in the formed hyperbaric chamber by monitoring the pressure in the chamber by means of the pressure sensor located in the Life Signs Sensor (13) and adding or relieving the pressure to maintain a desired level through the Interface Oxygen Line (14) which also contains the transmission means for the communication between the plurality of Life Signs Sensors (13) and the Life Signs and Pressure Microprocessor (8).

Additionally the Life Signs and Pressure Microprocessor (8) receives data transmitted from the Life Signs Sensors (13) of body and skin conditions that may indicate the formation of a PRU is imminent or that there are conditions of an existing PRU that is being aggravated. The Life Signs Sensors (13) may be comprised of any one or more of the following sensors: body temperature; blood oxygen saturation; presence of a purulent liquid or bleeding; transcutaneous microvascular dynamics using in vivo optical measurement by laser Doppler fluximetry (LDF), pulse oximetry, photoplethysmography (PPG) and/or diffuse reflectance spectroscopy; and the force of pressure on the user's skin being exerted by one or more of the surfaces supporting the user. The Life Signs and Pressure Microprocessor (8) receives a continuous data stream of information from the Life Signs Sensors (13) and evaluates the data for adjustments of the device and/or notification of care personnel. If the Life Signs and Pressure Microprocessor (8) detects a life sign or pressure change in an area at risk of PRU, etc., or in treatment there for, the Life Signs and Pressure Microprocessor (8) can automatically change or pulsate for a massage type motion the oxygen pressure within the Flexible Inflatable Tubes (9) by providing compressed oxygen from the Compressed Oxygen Source (2) through the Oxygen Line (3) through the internal valve and solenoid system in the Life Signs and Pressure Microprocessor (8) through a conduit in the Interface Oxygen Line (14) to the Flexible Inflatable Tubes (9). This process will in effect move and or massage the user to relieve the pressure and stimulate blood flow to the region detected by the device to be a problem. In the event that the device continues to detect the problem or a worsening condition the Life Signs and Pressure Microprocessor (8) will display the problem and simultaneously transmit the data and warning to a remote location such as a nurse's station or over the Internet.

In the design and use of this invention, the device can also be formed into the shape of any article of clothing or cuff, thereby reducing if not eliminating the need for multiple attachment means.

It would be obvious to one skilled in the art to manufacture my invention or parts thereof out of any other suitable material such as plastics, metals, ceramics or other composite materials. Similarly, my invention can be designed to sound alarms, display continuous data streams on the device of remotely, use other fluids to maintain pressure in the Flexible Inflatable Tubes (9) which could in turn could be heated or cooled for other medical applications. The device similarly could be fashioned into a sleeping surface or seat and backrest as may be used in a wheelchair setting.

While my above description of the invention, its parts, and operations contains many specificities, these should not be construed as limitations on the scope of the invention, but rather as exemplifications of present embodiments thereof. Many other variations are possible, for example, other embodiments, shapes, and sizes of the device can be constructed and designed to work by the principles of the present invention; various materials, colors and configurations can be employed in the device's design that would provide interesting embodiment differences to users.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. Accordingly, the scope of the invention should be determined not by the embodiments illustrated, but by the claims and their legal equivalents which accompany this application.

Having described my invention, I claim:

1. An oxygen healing system comprised of:
   a source of oxygen;
   a microprocessor connected to the source of oxygen wherein the microprocessor is capable of regulating a flow of oxygen from the source of oxygen;
   an inflatable garment formed from a flexible material to a user specified shape and size suitable to be worn by the user wherein the inflatable garment is connected to the microprocessor such that the inflatable garment may receive a flow of oxygen from the microprocessor thereby facilitating the inflation with oxygen of the inflatable garment by means of the microprocessor;
   at least one life signs sensor situated in a proximity close enough to a user's body to determine at least one life sign of the user wherein the life sign sensor is in electronic communication with the microprocessor wherein the microprocessor will permit the flow of oxygen from the oxygen delivery means to the inflatable garment at such pressure and quantity as the microprocessor determines is appropriate based upon user selected parameters and the data the microprocessor receives from the life sign sensor;
   at least one port disposed in the inflatable garment wherein the port permits a quantity of oxygen to escape from the inflated inflatable garment such that a pressure of oxygen greater than the atmospheric pressure is created and maintained thereby between the inflatable garment and the user when the oxygen healing system is in use; and
   a urine collection and disposal means wherein the urine collection and disposal means is further comprised of a urine sensor such that when the urine collection and disposal means is worn by a user and the user discharges urine, the urine sensor detects the presence of urine and thereby activates the urine collection and disposal means to collect the urine being discharged and dispose of the urine away from the user thereby minimizing the urine's contact with the user.

2. The oxygen healing system of claim 1 wherein the source of oxygen is at least one source selected from the group consisting of: a tank of compressed oxygen; an oxygen generator; or an oxygen valve and port such as used in a hospital or health care facility.

3. The oxygen healing system of claim 1 wherein the inflatable garment is further comprised of:
   a plurality of inflatable tubes connected to the microprocessor wherein the inflatable tubes may receive a flow of oxygen from the microprocessor thereby facilitating the inflation with oxygen of the inflatable tubes by means of the microprocessor;
   at least one valve connected to each of the inflatable tubes and the microprocessor wherein the pressure of oxygen in each of the inflatable tubes can be independently regulated by the microprocessor control of the valve in response to a manual setting of a user or in automatic response to the data the microprocessor receives from the life signs sensor thereby actuating at least one action selected from the group consisting of: a massage type motion of the inflatable tubes; an increase in oxygen pressure between the inflatable garment and the user in the proximity of specified inflatable tubes; a decrease in oxygen pressure between the inflatable garment and the user in the proximity of specified inflatable tubes; or a pulsation of the inflatable tubes.

4. The oxygen healing system of claim 3 wherein the life sign sensor is further comprised of a device capable of sensing and transmitting data regarding at least one of the life signs and data selected from the group consisting of: air pressure; ambient oxygen concentration; body temperature; blood oxygen saturation; presence of a purulent liquid or bleeding; transcutaneous microvascular dynamics using in vivo optical measurement by laser Doppler fluximetry (LDF), pulse oximetry, photoplethysmography (PPG), diffuse reflectance spectroscopy; or the force of pressure on the user's skin being exerted by one or more of the surfaces supporting the user.

5. A method of using the oxygen healing system of claim 4 consisting of the steps of:
   placing the inflatable garment in contact with a user selected area of the user's body;
   placing and then securing the urine collection and disposal means in a functional position near the genitalia of the user wherein when the user discharges urine the urine is collected and then the urine sensor detects the presence of urine and thereby activates the urine collection and disposal means to collect the urine being discharged and dispose of the urine away from the user thereby minimizing the urine's contact with the user;
   tightening the strap and securing it in the tightened position with the attachment means wherein the inflatable garment's proximity to the user's body is close enough to create a seal sufficient to permit a flow of oxygen from the ports to produce an amount of pressure of the oxygen between the user's body and the inflatable garment that is greater than the atmospheric pressure;
   connecting the microprocessor to the inflatable garment;
   connecting the microprocessor to the source of oxygen; and
   activating the microprocessor.

6. The oxygen healing system of claim 1 wherein the inflatable garment is held in functional proximity to the user by at least one strap held in place by an attachment means selected from the group consisting of: hooks and loops; snaps; buckles; buttons; or laces.

7. A method of using the oxygen healing system of claim 6 consisting of the steps of:
   placing the inflatable garment in contact with a user selected area of the user's body;
   placing and then securing the urine collection and disposal means in a functional position near the genitalia of the user wherein when the user discharges urine the urine is collected and then the urine sensor detects the presence of urine and thereby activates the urine collection and disposal means to collect the urine being discharged and dispose of the urine away from the user thereby minimizing the mine's contact with the user.
   tightening the strap and securing it in the tightened position with the attachment means wherein the inflatable garment's proximity to the user's body is close enough to create a seal sufficient to permit a flow of oxygen from the ports to produce an amount of pressure of the oxygen between the user's body and the inflatable garment that is greater than the atmospheric pressure;
   connecting the microprocessor to the inflatable garment;
   connecting the microprocessor to the source of oxygen; and
   activating the microprocessor.

8. An oxygen healing system comprised of:
a source of oxygen;
a microprocessor connected to the source of oxygen wherein the microprocessor is capable of regulating a flow of oxygen from the source of oxygen;
an inflatable garment formed from a flexible material to a user specified shape and size suitable to be worn by the user wherein the inflatable garment is connected to the microprocessor such that the inflatable garment may receive a flow of oxygen from the microprocessor thereby facilitating the inflation with oxygen of the inflatable garment by means of the microprocessor;
at least one life signs sensor situated in a proximity close enough to a user's body to determine at least one life sign of the user wherein the life sign sensor is in electronic communication with the microprocessor wherein the microprocessor will permit the flow of oxygen from the oxygen delivery means to the inflatable garment at such pressure and quantity as the microprocessor determines is appropriate based upon user selected parameters and the electronic information the microprocessor receives from the life sign sensor; and
at least one port disposed in the inflatable garment wherein the port permits a quantity of oxygen to escape from the inflated inflatable garment such that a pressure of oxygen greater than the atmospheric pressure is created and maintained thereby between the inflatable garment and the user when the oxygen healing system is in use.

9. The oxygen healing system of claim 8 wherein the source of oxygen is at least one source selected from the group consisting of: a tank of compressed oxygen; an oxygen generator; or an oxygen valve and port such as used in a hospital or health care facility.

10. The oxygen healing system of claim 8 wherein the inflatable garment is further comprised of:
a plurality of inflatable tubes connected to the microprocessor wherein the inflatable tubes may receive a flow of oxygen from the microprocessor thereby facilitating the inflation with oxygen of the inflatable tubes by means of the microprocessor;
at least one valve connected to each of the inflatable tubes and the microprocessor wherein the pressure of oxygen in each of the inflatable tubes can be independently regulated by the microprocessor control of the valve in response to a manual setting of a user or in automatic response to the data the microprocessor receives from the life signs sensor thereby actuating at least one action selected from the group consisting of: a massage type motion of the inflatable tubes; an increase in oxygen pressure between the inflatable garment and the user in the proximity of specified inflatable tubes; a decrease in oxygen pressure between the inflatable garment and the user in the proximity of specified inflatable tubes; or a pulsation of the inflatable tubes.

11. The oxygen healing system of claim 10 wherein the life sign sensor is further comprised of a device capable of sensing and transmitting data regarding at least one of the life signs and data selected from the group consisting of: air pressure; ambient oxygen concentration; body temperature; blood oxygen saturation; presence of a purulent liquid or bleeding; transcutaneous microvascular dynamics using in vivo optical measurement by laser Doppler fluximetry (LDF), pulse oximetry, photoplethysmography (PPG), diffuse reflectance spectroscopy; or the force of pressure on the user's skin being exerted by one or more of the surfaces supporting the user.

12. A method of using the oxygen healing system of claim 11 consisting of the steps of:
placing the inflatable garment in contact with a user selected area of the user's body;
tightening the strap and securing it in the tightened position with the attachment means wherein the inflatable garment's proximity to the user's body is close enough to create a seal sufficient to permit a flow of oxygen from the ports to produce an amount of pressure of the oxygen between the user's body and the inflatable garment that is greater than the atmospheric pressure;
connecting the microprocessor to the inflatable garment;
connecting the microprocessor to the source of oxygen; and
activating the microprocessor.

13. The oxygen healing system of claim 8 wherein the inflatable garment is held in functional proximity to the user by at least one strap held in place by an attachment means selected from the group consisting of: hooks and loops; snaps; buckles; buttons; or laces.

14. A method of using the oxygen healing system of claim 13 consisting of the steps of:
placing the inflatable garment in contact with a user selected area of the user's body;
tightening the strap and securing it in the tightened position with the attachment means wherein the inflatable garment's proximity to the user's body is close enough to create a seal sufficient to permit a flow of oxygen from the ports to produce an amount of pressure of the oxygen between the user's body and the inflatable garment that is greater than the atmospheric pressure;
connecting the microprocessor to the inflatable garment;
connecting the microprocessor to the source of oxygen; and
activating the microprocessor.

* * * * *